United States Patent [19]

Edwards, III et al.

[11] Patent Number: 4,561,451

[45] Date of Patent: Dec. 31, 1985

[54] 1,4-DIACYLPIPERAZINE FLAVORED SMOKING COMPOSITIONS

[75] Inventors: William B. Edwards, III; Yoram Houminer, both of Richmond, Va.

[73] Assignee: Philip Morris Incorporated, New York, N.Y.

[21] Appl. No.: 410,205

[22] Filed: Aug. 23, 1982

[51] Int. Cl.[4] .......................... A24B 3/12; A24B 15/38
[52] U.S. Cl. .................................... 131/278; 544/387
[58] Field of Search ................ 131/278, 310; 544/224, 544/336, 358, 386, 387; 424/40, 197; 260/96.5

[56] References Cited

U.S. PATENT DOCUMENTS

| | | | |
|---|---|---|---|
| 156,787 | 8/1874 | Hahn et al. | 131/310 |
| 1,334,752 | 3/1920 | Hagino et al. | 131/310 |
| 3,329,668 | 7/1967 | McKay | 260/96.5 |
| 3,365,454 | 1/1968 | Ferguson et al. | 260/268 |
| 3,402,051 | 9/1968 | Roberts | 131/278 |
| 4,137,305 | 1/1979 | Rowsell et al. | 424/54 |

Primary Examiner—V. Millin
Assistant Examiner—Gregory Beaucage

[57] ABSTRACT

This invention provides smoking compositions which contain a diacylpiperazine additive such as 1,4-(2-methylpropionyl)-2,3,5,6-tetramethylpiperazine:

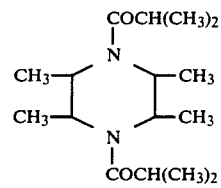

The preferred diacylpiperazine additives impart enhanced flavor response and smoothness.

8 Claims, No Drawings

1,4-DIACYLPIPERAZINE FLAVORED SMOKING COMPOSITIONS

BACKGROUND OF THE INVENTION

The incorporation of flavorants in tobacco products is an important development in the tobacco industry due to the lowered aromaticity of the available tobacco and the increased preference of smokers for filter cigarettes and low delivery cigarettes.

A variety of organic compounds have been developed and proposed for incorporation as flavorants into tobacco products. Illustrative of such tobacco flavorants are those described in U.S. Pat. Nos. 2,766,150; 3,180,340; 3,580,259; 3,625,224; 3,722,516; 3,750,674; 3,782,391; 3,854,485; 3,879,425; 3,881,025; 3,884,247; 3,890,981; 3,903,900; 3,914,451; 3,915,175; 3,920,027; 3,924,644; 3,937,228; 3,943,943; 3,586,387; and the like. The tobacco flavorants include compounds such as succinic anhydride; dihydroxyacetone; substituted pyridines; cinnamic derivatives; isovaleric acid; 6-methylhepta-3,5-dien-2-one; 2-butyl-2-butenal; 1,3-cyclohexadiene; alpha-pyrones; substituted butyrolactones; pyrazines and thiazolidines; and the like.

Of interest with respect to the present invention are various tobacco constituents which have been isolated and identified, as reported in Tobacco Science, 20, 43 (1976). Tobacco constituents having organoleptic properties include pyrrolidine derivatives of the following structure:

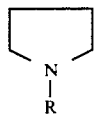

where R is $CHO$, $COCH_3$ or $COCH_2CH(CH_3)_2$.

There is continuing research effort directed to the development of novel compounds which exhibit properties suitable for application as flavorants in edible and topical preparations and in smoking compositions.

Accordingly, it is an object of this invention to provide novel piperazine derivatives which exhibit flavorant properties.

It is a further object of this invention to provide smoking compositions which have incorporated an additive which exhibits flavorant properties under smoking conditions.

Other objects and advantages of the present invention shall become apparent from the accompanying description and examples.

DESCRIPTION OF THE INVENTION

One or more objects of the present invention are accomplished by the provision of a smoking composition comprising an admixture of (1) combustible filler selected from natural tobacco, reconstituted tobacco, non-tobacco substitutes, and mixtures thereof, and (2) between about 0.00001 and 2 weight percent, based on the total weight of filler, of a diacylpiperazine additive corresponding to the formula:

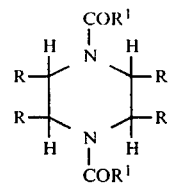

where R is hydrogen or an alkyl substituent containing between about 1-8 carbon atoms, and $R^1$ is a hydrocarbyl group containing between about 1-12 carbon atoms.

R in the diacylpiperazine formula is selected from substituents which include hydrogen, methyl, ehtyl, propyl, 2-methylpropyl, pentyl, 2-ethylhexyl, and the like.

$R^1$ in the diacylpiperazine formula is selected from substituents which include methyl, ethyl, 1-propenyl, butyl, 2-ethylhexyl, decyl, cyclohexyl, phenyl, and the like. The $R^1$ substituents can also be oxygen-containing such as 2-methoxyethyl, 4-methoxyphenyl, and the like.

For purposes of the present invention, the preferred diacylpiperazine compounds are those in which $R^1$ contains at least two carbon atoms. Such compounds are advantageous in that they are less volatile, and tend to exhibit favorable flavorant properties under smoking conditions. Thus, in another embodiment this invention provides novel diacylpiperazine compounds as per the formula above in which each $R_1$ substituent contains two or more carbon atoms, such as 1,4-dipropionyl-2-methylpiperazine and 1,4-di(2-methylpropionyl)piperazine.

In a further embodiment this invention provides diacylpiperazine compounds as per the formula above which contain at least two R substituents, such as 1,4-dipropionyl-2,5-dimethylpiperazine.

As illustrated in the Examples, diacylpiperazine compounds can be synthesized by the interaction of appropriately selected acyl halide and piperazine reactants to provide compounds in accordance with the formula above.

PREPARATION OF TOBACCO COMPOSITIONS

This invention further provides a method of preparing a smoking compositions which is adapted to impart flavoring to the mainstream and sidestream smoke under smoking conditions, which method comprises incorporating into natural tobacco, reconstituted tobacco, non-tobacco substitute or mixtures thereof between about 0.00001 and 2 weight percent, based on composition weight, of diacylpiperazine additive corresponding to the formula:

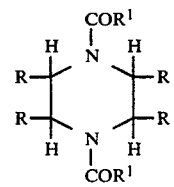

where R is hydrogen or an alkyl substituent containing between about 1-8 carbon atoms, and $R^1$ is a hydrocarbyl group containing between about 1-12 carbon atoms.

An invention diacylpiperazine additive can be incorporated into the tobacco in accordance with methods known and used in the art. Preferably the flavorant additive is dissolved in a solvent such as water, alcohol or mixtures thereof, and then sprayed or injected into the tobacco or non-tobacco substitute matrix. Such method ensures an even distribution of the additive throughout the tobacco, and thereby facilitates the production of a more uniform smoking composition. Alternatively, the flavorant additive may be incorporated as part of a concentrated tobacco extract which is applied to a fibrous tobacco web as in the manufacture of reconstituted tobacco. Another suitable procedure is to incorporate the additive in tobacco or non-tobacco substitute filler in a concentration between about 0.005–5 weight percent, based on the weight of filler, and then subsequently to blend the treated filler with filler which does not contain additive.

The term "non-tobacco substitute" is meant to include smoking filler materials such as are disclosed in U.S. Pat. Nos. 3,529,602; 3,703,177; 3,796,222; 4,019,521; 4,079,742; and references cited therein; incorporated herein by reference.

Illustratively, U.S. Pat. No. 3,529,602 describes a burnable sheet which may be used as a tobacco substitute, which sheet contains ingredients which include (1) a film-forming ingredient comprising a pectinaceous material derived from tobacco plant parts and having an acid value in excess of 30 milligrams of potassium hydroxide per gram, and (2) a mineral ingredient comprising an alkali metal salt, an alkaline earth metal salt or clay.

U.S. Pat. No. 3,703,177 describes a process for preparing a non-tobacco smoking product from sugar beet pulp, which process involves the acid hydrolysis of the beet pulp to release beet pectins, and at least an alkaline earth treatment thereafter to cause crosslinking of the pectins and the formation of a binding agent for the exhausted beet matrix.

U.S. Pat. No. 3,796,222 describes a smoking product derived from coffee bean hulls. The hulls are treated with reagents that attack the alkaline earth metal crosslinks causing the release of the coffee pectins. The pectins act as a binding agent and together with the treated hulls may be handled and used similarly to a tobacco product.

U.S. Pat. No. 4,019,521 discloses a process for forming a smoking material which involves heating a cellulosic or carbohydrate material at a temperature of 150°–750° C. in an inert atmosphere for a period of time sufficient to effect a weight loss of at least 60 percent but not more than 90 percent.

U.S. Pat. No. 4,079,742 discloses a process for the manufacture of a synthetic smoking product from a cellulosic material, which process involves a pyrolysis step and a basic extraction step to yield a resultant matrix which has a tobacco-like brown color and has improved smoking characteristics.

When a present invention diacylpiperazine compound is incorporated into smoking material as an additive, and cigarettes are manufactured from the flavored blend, under smoking conditions the cigarette taste generally has more response and smoothness and increased flavor amplitude in comparison with control cigarettes which do not contain the invention diacylpiperazine additive.

As indicated previously, particularly advantageous are smoking compositions which contain a diacylpiperazine additive as per the formula above in which each $R^1$ contains at least two carbon atoms. The superior flavorant properties of the preferred compounds are demonstrated in subjective testing by an experienced smoking panel in which 1,4-diacetyl-2-methylpiperazine is judged to have an oily, thin and sharp taste when contained as a flavorant in cigarettes under smoking conditions, and 1,4-di(2-methylpropionyl)-2,3,5,6-tetramethylpiperazine is indicated as having a smoother and milder taste than control cigarettes.

The following examples are further illustrative of the present invention. The reactants and other specific ingredients are presented as being typical, and various modifications can be derived in view of the foregoing disclosure within the scope of the invention.

EXAMPLE I 1,4-Diacetyl-2-methylpiperazine

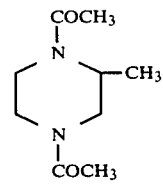

To a cooled stirring solution of 5.0 g (0.05 mole) of 2-methylpiperazine and 11.13 g (0.11 mole) of triethylamine in 200 ml of dichloromethane under nitrogen is added a 8.6 g (0.11 mole) quantity of acetyl chloride in 50 ml of dichloromethane over a period of about an hour. The resulting mixture is stirred overnight at room temperature. Insoluble solid is removed by filtration and the filtrate is washed with saturated aqueous sodium chloride, and then with 5% aqueous hydrogen chloride and with saturated aqueous sodium chloride. The dichloromethane solution is dried (magnesium sulfate) and the solvent removed to provide 4.75 g of a solid.

The solid is recrystallized from benzene and then dried over phosphorus pentoxide in vacuo for four hours to yield 2.73 g of 1,4-diacetyl-2-methylpiperazine: mp, 116°–117.5° C. The product structure is confirmed by IR and NMR spectroscopic analysis.

EXAMPLE II

2-Methyl-1,4-dipentanoylpiperazine

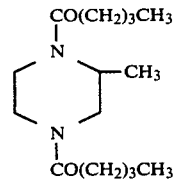

To a cooled stirring solution of 5 g (0.05 mole) of 2-methylpiperazine and 13.15 g (0.13 mole) of triethylamine in 250 ml of dichloromethane under a nitrogen atmosphere is added a 15.68 g (0.13 mole) quantity of pentanoyl chloride in 50 ml of dichloromethane over a period of about one hour. The reaction is allowed to stir at room temperature for 3 days. Insoluble solid is removed by filtration and washed with dichloromethane. The combined filtrates are washed with water and then stirred with 50 ml of water and 10 ml of saturated aqueous sodium bicarbonate for 2 hours. The dichloromethane layer is separated and washed consecutively with saturated aqueous sodium bicarbonate, 10% aqueous hydrogen chloride and saturated aqueous sodium chloride. The dichloromethane solution is dried (magnesium sulfate) and the solvent is removed under reduced pressure to provide 15.18 g of a semi-solid.

Preparative high pressure liquid chromatography [silicic acid, dichloromethane/ethyl acetate (1:1)] of a portion of the semi-solid yields a solid. Bulb to bulb distillation (oven temperature range 120°-130° C., 0.03 mm/Hg) of this solid affords 2-methyl-1,4-dipentanoylpiperazine as a clear oil. IR and NMR spectroscopic analysis confirm the product's structure.

EXAMPLE III 2,5-Dimethyl-1,4-dipropionylpiperazine

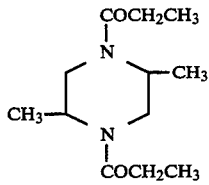

To a cooled stirring solution of 5 g (0.004 mole) of 2,5-dimethylpiperazine and 11.5 g (0.114 mole) of triethylamine in 150 ml dichloromethane under a nitrogen atmosphere is added a 10.6 g (0.114 mole) quantity of propionyl chloride in 50 ml of dichloromethane over a period of about one hour. The reaction is allowed to stir at room temperature for 3 days. Insoluble solid is removed by filtration and washed with dichloromethane. The combined filtrates are washed with water and then stirred with 50 ml of water and 10 ml of saturated aqueous sodium bicarbonate for 2 hours. The dichloromethane layer is separated and washed consecutively with saturated aqueous sodium bicarbonate, 10% aqueous hydrogen chloride and saturated aqueous sodium chloride. The dichloromethane solution is dried (magnesium sulfate) and the solvent is removed under reduced pressure to leave a solid. The solid is washed with hexane, recrystallized from hexane/acetone, and dried in vacuo for 16 hours at 55° C. over phosphorus pentoxide to yield 4.11 g of 2,5-dimethyl-1,4-dipropionylpiperazine: mp, 130°-131° C., as confirmed by IR and NMR spectroscopic analysis.

The use of benzoyl chloride as a reactant in the above procedure provides the corresponding 2,5-dimethyl-1,4-dibenzoylpiperazine product. A mixture of benzoyl chloride and propionyl chloride yields a diacylpiperazine product mixture containing benzoyl-benzoyl, propionyl-propionyl and benzoyl-propionyl 1,4-disubstituted compounds.

EXAMPLE IV 1,4-Dibutyryl-2,5-dimethylpiperazine

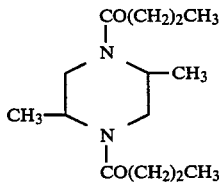

The reaction of 5 g (0.044 mole) of 2,5-dimethylpiperazine with 12.15 g (0.0114 mole) of butyryl chloride is conducted as described in Example III, and the crude product obtained is an oily solid. The solid is washed with hexane, recrystallized from hexane/acetone, and dried in vacuo for 16 hours at 55° C. over phosphorus pentoxide to yield 6.47 g of 1,4-dibutryl-2,5-dimethylpiperazine: mp, 92°-94° C., as confirmed by IR and NMR spectroscopic analysis.

The use of ethoxyacetyl chloride as a reactant in the above procedure provides the corresponding 1,4-diethoxyacetyl-2,5-dimethylpiperazine product.

EXAMPLE V

2-Ethyl-1,4-di(2-methylpropionyl)piperazine

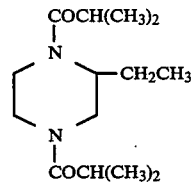

A mixture of 7.0 g (0.065 mole) of ethylpyrazine, 0.7 g of 10% palladium on carbon and 100 ml of ethanol are shaken under a hydrogen atmosphere at about 50 psi and room temperature for 2 days. The mixture is filtered and 0.7 g of 10% palladium on charcoal is added. The mixture is shaken under a hydrogen atmosphere at about 50 psi and room temperature for 2 days. The resultant product mixture is filtered and the ethanol removed under reduced pressure to leave an oil. The oil is distilled under reduced pressure to yield 4.8 g of 2-ethylpiperazine: mp, 59°-60° C.

The reaction of 4.7 g (0.041 mole) of 2-ethylpiperazine with 11.4 g (0.107 mole) of 2-methylpropionyl chloride is conducted as described in Example III, and an oil is obtained. Bulb to bulb distillation under reduced pressure (0.15 mm/Hg) is carried out on a 2 g portion of the oil. The material collected over the oven temperature range 120°-130° C. solidified on scratching. It was dried in vacuo (0.05 mm/Hg) for 16 hours over phosphorus pentoxide at room temperature, and 5 hours over sodium hydroxide at 50° C. to afford 1.3 g of 2-ethyl-1,4-di(2-methylpropionyl)piperazine: mp, 70°-73° C., as confirmed by IR and NMR spectroscopic analysis.

EXAMPLE VI 1,4-Di(2-methylpropionyl)-2,5-dimethylpiperazine

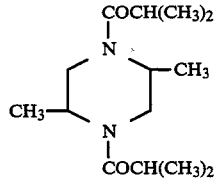

To a cooled, stirring solution of 5.7 g (0.05 mole) of 2,5-dimethylpiperazine in 150 ml of dichloromethane containing 13.15 g (0.13 mole) of triethylamine is added a solution of 13.85 g (0.13 mole) of 2-methylpropionyl chloride in 50 ml of dichloromethane. The resulting mixture is stirred at room temperature for 3 days. Insoluble solid is removed by filtration and washed with dichloromethane. The combined filtrates are stirred with 50 ml of water and 10 ml of saturated aqueous sodium carbonate for one hour. The organic layer is washed with a sodium carbonate solution followed by 10% hydrochloric acid and water washes. The solution is dried over magnesium sulfate and the solvent is removed under reduced pressure to yield 12.0 g of a solid. Recrystallization of the solid from acetone yields 6.6 g of the pure product: mp, 175°–177° C. The structure is confirmed by spectroscopic analysis.

EXAMPLE VII 1,4-Di(2-methylpropionyl)-2,6-dimethylpiperazine

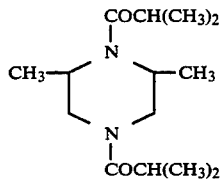

The reaction of 5.7 g (0.05 mole) of 2,6-dimethylpiperazine with 13.85 g (0.13 mole) of 2-methylpropionyl chloride is carried out as described in Example VI, and yields 13.3 g of crude product as a solid. Recrystallization from acetone provides 7.1 g of the pure product: mp, 160°–161° C. An additional 4.0 g of pure product is obtained by concentrating the mother liquor and adding hexane. The assigned product structure is consistent with IR and NMR data.

EXAMPLE VIII 1,4-Di(2-methylpropionyl)-2-methylpiperazine

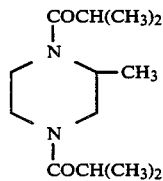

Using the procedure of Example VI, the interaction of 2-methylpiperazine with 2-methylpropionyl chloride yields a solid product: mp, 120°–121° C. IR and NMR data confirm the above indicated structure.

EXAMPLE IX 1,4-Di(2-methylpropionyl)-2,3,5,6-tetramethylpiperazine

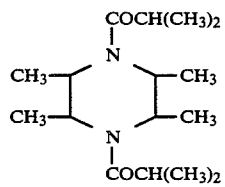

Using the procedure of Example VI, the interaction of 2,3,5,6-tetramethylpiperazine with 2-methylpropionyl chloride yields a solid product: mp, 145°–158° C. IR and NMR data confirm the above indicated structure.

EXAMPLE X

This Example illustrates the preparation of present invention smoking compositions.

Cigarettes are fabricated employing a blend of tobacco treated with an ethanolic solution of a diacylpiperazine additive to provide a tobacco with a 100–500 ppm concentration of additive. The cigarettes are targeted to deliver 3–16 mg of tar per cigarette.

Untreated controls are prepared and the treated cigarettes are compared to the controls by an experienced smoking panel:

|  | Additive | Subjective Taste Results vs. Control |
|---|---|---|
| Ex. I | COCH₃ piperazine structure with CH₃ and COCH₃ | More oily, thin and sharp. |
| Ex. II | CO(CH₂)₃CH₃ piperazine structure with CH₃ and CO(CH₂)₃CH₃ | More response; slight harshness; more taste. |
| Ex. VI | piperazine structure with COCH(CH₃)₂, CH₃ (×2), COCH(CH₃)₂ | Less response; tobacco flavor; more smoothness. |
| Ex. VII | piperazine structure with COCH(CH₃)₂, CH₃ (×2), COCH(CH₃)₂ | More response; more tobacco-like; smoother. |
| Ex. IX | piperazine structure with COCH(CH₃)₂, CH₃ (×4), COCH(CH₃)₂ | Smoother and milder. |

What is claimed is:

1. A smoking composition comprising an admixture of (1) combustible filler selected from natural tobacco, reconstituted tobacco, non-tobacco substitutes, and mixtures thereof, and (2) between about 0.00001 and 2 weight percent, based on the total weight of filler, of a diacylpiperazine flavorant additive corresponding to the formula:

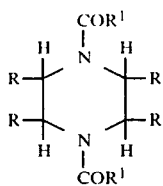

where R is hydrogen or an alkyl substituent containing between about 1-8 carbon atoms and at least two R substituents are alkyl groups, and $R^1$ is a hydrocarbyl group containing between about 2-12 carbon atoms.

2. A smoking composition in accordance with claim 1 wherein the non-tobacco substitutes are selected from pectinaceous, cellulosic and carbohydrate materials.

3. A smoking composition in accordance with claim 1 wherein the diacylpiperazine additive is 2,5-dimethyl-1,4-dipropionylpiperazine.

4. A smoking composition in accordance with claim 1 wherein the diacylpiperazine additive is 1,4-dibutyryl-2,5-dimethylpiperazine.

5. A smoking composition in accordance with claim 1 wherein the diacylpiperazine additive is 1,4-di(2-methylpropionyl)-2,5-dimethylpiperazine.

6. A smoking composition in accordance with claim 1 wherein the diacylpiperazine additive is 1,4-di(2-methylpropionyl)-2,6-dimethylpiperazine.

7. A method of preparing a smoking composition which is adapted to impart flavoring to the mainstream and sidestream smoke under smoking conditions, which method comprises incorporating into natural tobacco, reconstituted tobacco, non-tobacco substitute or mixtures thereof between about 0.00001 and 2 weight percent, based on composition weight, of diacylpiperazine flavorant additive corresponding to the formula:

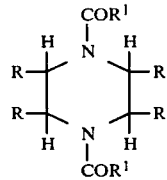

where R is hydrogen or an alkyl substituent containing between about 1-8 carbon atoms and at least two R substituents are alkyl groups, and $R^1$ is a hydrocarbyl group containing between about 2-12 carbon atoms.

8. A smoking composition comprising an admixture of (1) combustible filler selected from natural tobacco, reconstituted tobacco, non-tobacco substitutes, and mixtures thereof, and (2) between about 0.00001 and 2 weight percent, based on the total weight of filler, of 1,4-di(2-methylpropionyl)-2,3,5,6-tetramethylpiperazine additive.

* * * * *